United States Patent
Basch et al.

[11] Patent Number: 6,138,521
[45] Date of Patent: *Oct. 31, 2000

[54] SEQUENTIAL AIR SAMPLER WITH AUTOMATIC SAMPLE COLLECTOR CHANGER

[75] Inventors: Lauren R. Basch, East Greenbush; Harvey Patashnick, Voorheesville, both of N.Y.

[73] Assignee: Rupprecht & Patashnick Company, Inc., Albany, N.Y.

[*] Notice: This patent is subject to a terminal disclaimer.

[21] Appl. No.: 09/457,941

[22] Filed: Dec. 9, 1999

Related U.S. Application Data

[63] Continuation of application No. 09/071,609, May 1, 1998, Pat. No. 6,023,982.

[51] Int. Cl.$^7$ ............................................. G01N 1/24
[52] U.S. Cl. .......................................... 73/863.25
[58] Field of Search .................. 73/863.01, 863.11, 73/863.21–863.23, 863.25, 864.31, 864.34, 864.71

[56] References Cited

U.S. PATENT DOCUMENTS

| | | | |
|---|---|---|---|
| 2,348,806 | 5/1944 | Gillard et al. | 73/863.11 |
| 3,074,276 | 1/1963 | Moos | 73/864.71 |
| 3,657,920 | 4/1972 | Teel et al. | 73/28 |
| 4,257,266 | 3/1981 | Apple | 73/863.01 |
| 4,577,518 | 3/1986 | Fong et al. | 73/863.01 |
| 4,584,887 | 4/1986 | Galen | 73/863.31 |
| 4,628,748 | 12/1986 | Jogan et al. | 73/864.34 |
| 5,553,507 | 9/1996 | Basch et al. | 73/863.01 |
| 5,571,946 | 11/1996 | Koshi et al. | 73/28.01 |
| 5,717,147 | 2/1998 | Basch et al. | 73/863.23 |
| 6,023,982 | 2/2000 | Basch et al. | 73/863.25 |

FOREIGN PATENT DOCUMENTS

| | | |
|---|---|---|
| 40 41 609 A1 | 6/1992 | Germany. |
| 195 03 663 A1 | 8/1995 | Germany. |
| 295 16 609 U1 | 10/1995 | Germany. |
| WO 94/29716 | 12/1994 | WIPO. |

OTHER PUBLICATIONS

High Vol. Dust–Sampler, Digitel Electronik, Hebnau, Germany, (15 pp.) 1995—partially in English.
Product Specification Sheet, Partisol–FRM Plus Model 2025 Sequential Air Sampler, 1996 (2 pp.).
A Sampling System for Reactive Species in the Western U.S., Chow et al. 1990 (19 pp.).
Features Sheet, partisol–FRM Plus Model 2025 Sequential Air Sampler, 1996 (2 pp.).
Patent Abstracts of Japan, JP 55127304, Publication No. 57052879, Mar. 29, 1982.

*Primary Examiner*—Robert Raevis
*Attorney, Agent, or Firm*—Heslin & Rothenberg, P.C.

[57] ABSTRACT

An air sampler having an automatic sample collector changer includes a supply magazine for holding a supply of fresh sample collectors and a receiving magazine for receiving and storing used collectors located aside a sampling station. A transfer mechanism transfers a fresh collector from the supply magazine to the sampling station and a used collector from the sampling station to an entrance of the receiving magazine. An automatic closer or plunger closes the entrance of the receiving magazine following transfer thereto of a used collector. The supply magazine can include an actuator for displacing a stack of sample collectors contained in said magazine. This stack may include interspersed air impervious covers. The transfer mechanism can transfer both a sample collector and a cover to the receiving magazine. Interspersing of covers with used sample collectors in the receiving magazine reduces volitization losses. For the same purpose, the temperature of the receiving magazine can be controlled. Preferably, all actuators of the sample collector changer are powered by a common vacuum pump which also serves to draw air into the sampling station for air sampling.

16 Claims, 8 Drawing Sheets

DIRECTION OF TRAVEL

SEQUENTIAL AIR SAMPLER WITH AUTOMATIC SAMPLE COLLECTOR CHANGER

This application is a continuation of prior application Ser. No. 09/071,609, filed May 1, 1998, now U.S. Pat. No. 6,023,982.

TECHNICAL FIELD

This invention relates generally to sampling of air and other gaseous media for particulate matter and other chemical species. More particularly, the present invention is directed to a sequential air sampler having an automatic sample collector changer.

BACKGROUND ART

Health concerns and related government regulations are prompting widespread use of air samplers to monitor particulate matter and other chemical species in the atmosphere. The majority of monitoring sites employ samplers operating under United States Environment Protection Agency regulations for filter sampling procedures. Filter samplers are place in the field and a constant flow of air through a preweighed filter is maintained for a set period of time, typically 24 hours. A technician visits the site after the sampling time period is completed and places a new filter in the sampler while retrieving the used filter. The used filter is brought to a laboratory where it is placed under specified constant conditions of temperature and humidity for 24 hours, and then weighed.

A major limitation of most of these samplers is that they only accommodate a single filter, requiring frequent visits to the site to change filters or multiple samplers located at the same site and timed to sample sequentially. Such solutions are expensive to implement. Presently available multiple filter sequential samplers attempt to address these problems, but do so in a way that present other difficulties both in mechanical complexity and contamination opportunities presented by unprotected filter storage within the air sampling instrument.

A need thus persists for an air sampler which can collect samples over multiple sampling periods without requiring manual intervention, involving undue mechanical complexity or compromising the air sampling process.

DISCLOSURE OF THE INVENTION

The present invention satisfies this need, overcomes the limitations of the prior art, and provides other benefits through the provision of an air sampler having a simple, reliable automatic sampler collector changer. According to the principles of the present invention, an air sampler includes a supply magazine for the supply of multiple fresh sample collectors and a closable receiving magazine for the reception and storage of used sample collectors. Transfer of a sample collector from the supply magazine to a sampling station and then on to the receiving magazine is preferably accomplished through pneumatic actuation resulting in simple and reliable transport. The magazines can be closed against both passive contamination and contamination introduced through handling while providing for easy attachment and detachment of the supply and receiving magazines containing multiple sample collectors. Potential cross contamination of sample collectors within the receiving magazine can be prevented by utilizing air impervious covers interspersed between stacked sample collectors. The temperature of the receiving magazine can also be controlled to reduce volitization losses.

In accordance with a first aspect of the present invention, an air sampler having an automatic sample collector changer includes a sampling station for sampling air to collect a sample on a sample collector, a supply magazine for holding a supply of fresh sample collectors, and a receiving magazine for receiving and storing used collectors from said sampling station following air sampling. A transfer mechanism transfers a fresh collector from the supply magazine to the sampling station and a used collector from the sampling station to an entrance of the receiving magazine. An automatic closer advantageously closes the entrance of the receiving magazine following transfer thereto of a used collector. Such closure protects the used sample collectors in the receiving magazine from contamination.

Preferably, the supply magazine holds a stack of fresh sample collectors, and includes an actuator for displacing the stack so as to provide an individual sample collector to the transfer mechanism for transfer to the sampling station. This actuator is preferably pneumatically driven by a pump which also serves to draw air into the sampling station for air sampling.

The supply magazine can hold a stack of sample collectors with interspersed or interleaved air impervious covers. Each sample collector may, for example, comprise a cassette having a screen for supporting a filter medium, and each cover could comprise a similarly sized air impervious cassette. In this embodiment, the transfer mechanism transfers a used sample collector and a cover to the receiving magazine following air sampling.

The supply magazine may comprise a cylindrical canister or tube with a pneumatic actuator, e.g. a piston located within said canister at one end thereof. Quick connect/disconnect means, e.g. a bayonet lock, can be provided at an opposite end of the canister to facilitate rapid attachment/detachment of the supply magazine relative to the sampling station. The supply magazine is preferably interchangeable with the receiving magazine and can be substituted therefor, when the receiving magazine is full.

The receiving magazine can be maintained at a set temperature by a temperature controller. The temperature controller may, for example, maintain the receiving magazine at a set temperature below ambient air temperature in order to reduce volitization losses from used sample collectors within the receiving magazine.

The transfer mechanism of the air sampler preferably comprises a pneumatically driven shuttle for transferring a fresh sample collector from the supply magazine to the sampling station. Advantageously, the pneumatically driven shuttle can be powered by the same pump that serves to draw air into the sampling station for air sampling purposes. The transfer mechanism can also include a spring-loaded kicker cam to transfer a used sample collector from the sampling station to the entrance of the receiving magazine. A further actuator can be employed to open the sampling station to allow transfer of a fresh sample collector into the station and transfer of a used sample collector out of the station. Another actuator may push a used sample collector into the receiving magazine. A plunger located at an end of the latter actuator serves to close the entrance of the receiving magazine. All of the actuators are preferably pneumatically driven from a common pump which alternately actuates the air sampling station. The receiving magazine can store used sample collectors as a stack with interspersed or interleaved air impervious covers.

In another aspect of the invention, the transfer mechanism transfers a fresh sample collector from the supply magazine to the sampling station, and the transferring fresh collector, in turn, displaces a used collector from the sampling station towards the entrance of the receiving magazine.

Other significant features of the present invention include, but are not limited to, the use of a common pump to alternately actuate the sample collector transfer mechanism and the sampling station, the incorporation of an actuator within the supply magazine, and the selective transfer of air impervious covers by the transfer mechanism to the receiving magazine. Further, such features can be readily automated under control of the processor or controller of the air sampler.

BRIEF DESCRIPTION OF THE DRAWINGS

These and other objects, advantages and features of the present invention will be more readily understood from the following detailed description of certain preferred embodiments, when considered in conjunction with the accompanying drawings in which.

DETAILED DESCRIPTION

Figure 1:
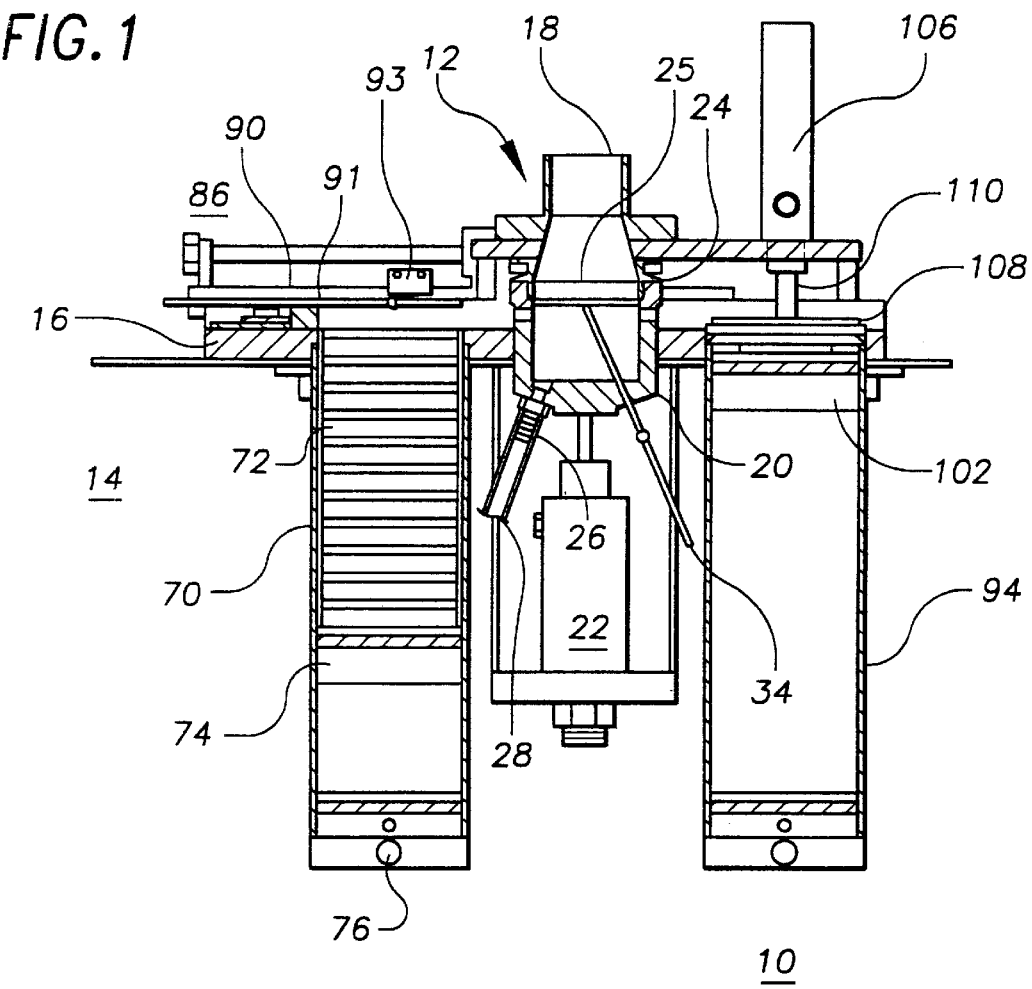
FIG. 1 is a side-sectional view of an air sampling station and automatic sample collector changer of an air sampler constructed in accordance with the principles of the present invention.

Referring now to the drawings in which the same reference numbers are used throughout multiple figures to designate the same or similar components, FIG. 1 depicts an air sampler 10 having a sampling station 12 and an automatic sample collector changer 14, in accordance with the principles of the present invention.

Sampling station 12 and sample collector changer 14 are mounted to a support structure or housing 16 of the air sampler.

Sampling station 12 includes a fixed upper holder 18 and a vertically displaceable lower holder 20. An actuator 22 mounted from and below support structure 16 positions lower holder 20 in either a retracted position spaced apart from upper holder 18 or an elevated position for creating a seal 24 about a sample holder 25 positioned within the sampling station for air sampling. Actuator 22 is preferably an air cylinder pneumatically driven by a common pump of the air sampler.

A fitting 26 joins hose 28 to the interior cavity of sampling station 12. As more fully described below, hose 28 is connected in a sampling train 30 to a standard vacuum pump 32 of the air sampler. In conventional fashion, the pump draws air into the sampling station 12 for air sampling and sample collection on sealed collector 25. A temperature probe 34 can be used to sense the temperature in the vicinity of collector 25.

Figure 3:
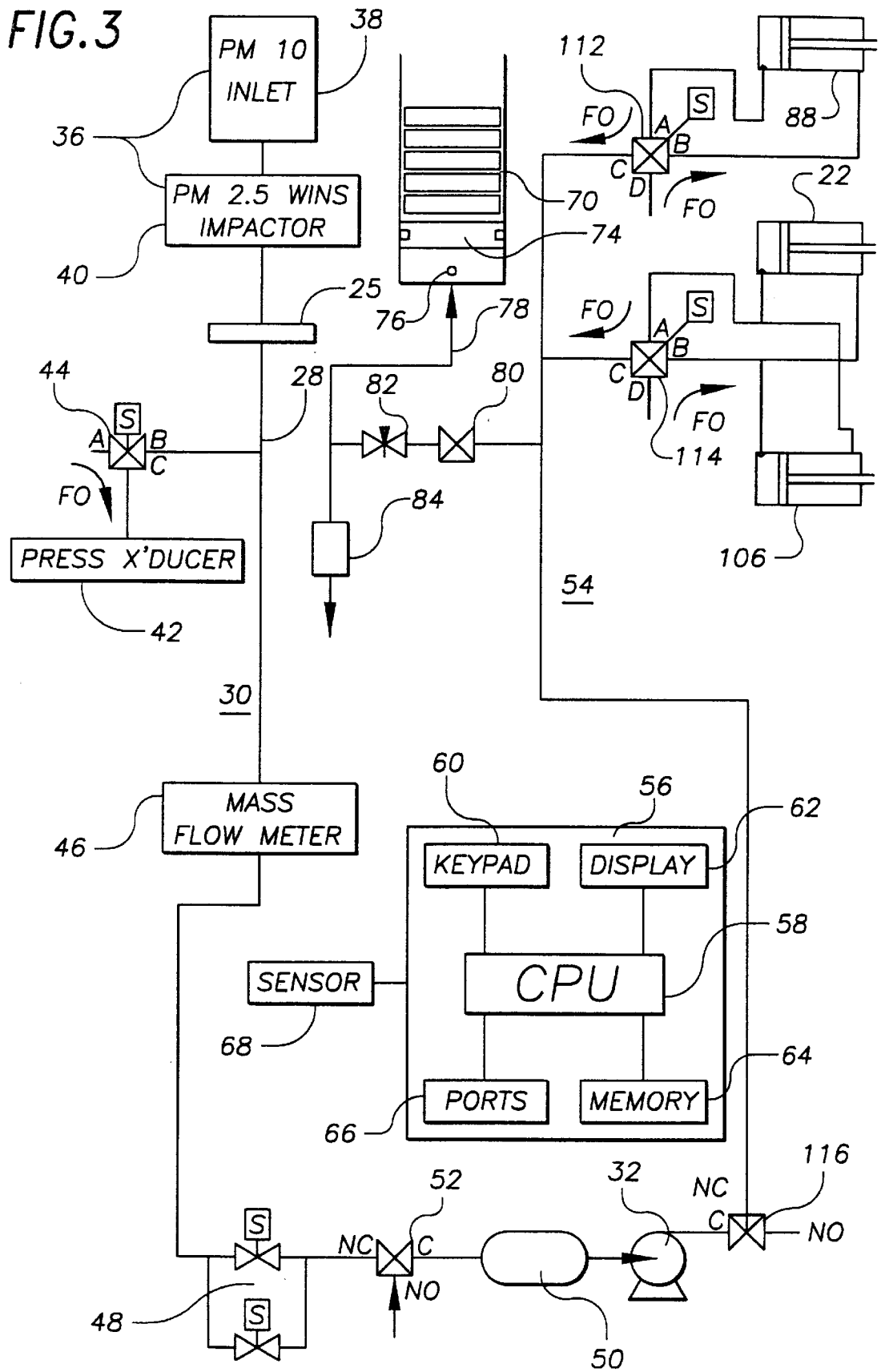
FIG. 3 illustrates a pneumatic circuit and other features of the air sampler of FIG. 1.

As shown in FIG. 3, sampling train 30 might typically also include an inlet assembly 36, e.g. a PM 10 (10 ppm) Inlet 38 and a PM 2.5 WINS Impactor 40 upstream of sampling station 12. Such an inlet assembly is well known and commercially available, and serves to segregate particles of a particular desired cut point.

Downstream of sampling station 12, a pressure transducer 42 can be connected to the sampling train via a three-way valve 44. Pressure transducer 42 measures either barometric pressure or absolute pressure in the system. A mass flow meter 46 is also preferably positioned along sampling 30. The mass flow meter may comprise a flow sensor and throttling valve operating under computer control. The mass flow meter, and ambient temperature and pressure sensors facilitate automatic volumetric flow control to maintain a constant desired volumetric flow rate through sampling station 12, in known fashion.

Sampling train 30 may also include proportional valves 48, an accumulator 50 and a vacuum pump 32. These components are conventional and their operation in an air sampler is well known. Finally, the sampling train is provided with a three-way vacuum vent valve 52 which advantageously allows pump 32 to alternately power sampling train 30 and an actuator valve train 54, as described more fully hereinafter.

As is well known in this art, the operation of sampling train 30 can be controlled by a microprocessor or controller 56 associated with the air sampler. Controller 56 typically includes a CPU 58 with a keypad 60 or other input device, a display 62, memory 64 and communication ports 66 connected thereto. Sensors 68 for both the sampling train 30 and actuator valve train 54 can also be connected to controller 56. In conventional fashion, controller 56 can be programmed to automate the operation of the air sampler so that sampling may occur over sequential sampling periods using a plurality of automatically exchanged sample collectors 25.

Referring again to FIG. 1, sample collector changer 14 includes a supply magazine 70 loaded with a stack 72 of fresh sample collectors 25. Sample collectors 25 may comprise filter cassettes, e.g. a 47 mm. filter supported by a perforated metal screen in a convenient, reusable cassette. Supply magazine 70 can then take the form of a cylindrical canister or tube with a diameter slightly larger than the cassette's.

Supply magazine 70 preferably includes an actuator 74, e.g. a pneumatically actuated piston, for selectively displacing stack 72 upwardly along the longitudinal axis of the magazine. A quick connect fitting 76 and associated hose 78 connect actuator 74 to the actuator valve train 54, as shown in FIG. 3. Actuator 74 is driven in response to controller activation of magazine pressurized valve 80. The pneumatic circuit also includes a flow limiter 82, e.g. a needle valve, and a relief valve 84. These components are conventional; their operation is described more fully hereinafter.

Figure 2:
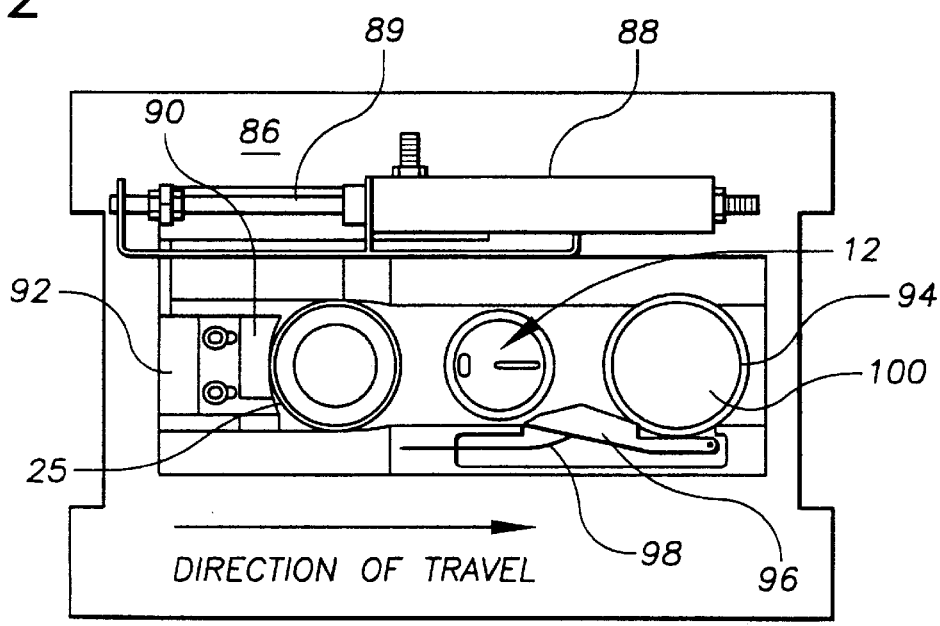
FIG. 2 is a top-plan view illustrating a transfer mechanism of the air sampler of FIG. 1.

Returning again to FIG. 1, changer 14 further includes a transfer mechanism generally denoted 86. Transfer mechanism 86 transfers or moves a fresh sample collector 25 at the top of stack 72 laterally into open sampling station 12. As best seen in the top view of FIG. 2, transfer mechanism 86 includes an actuator 88, e.g. an air cylinder, the piston 89 of which is connected to a shuttle 90 by a bracket 92. As piston 89 retracts, shuttle 90 moves from a home position inward towards sampling station 12. This movement conveys a sample collector 25 from the top of stack 72 above supply magazine 70 to a sampling position within open sampling station 12. The transferring fresh collector contacts a used collector in the sampling station from the prior sampling period and displaces the used collector in the direction of a receiving magazine 94. A pivotally mounted kicker cam 96 spring-loaded by a cam spring 98 is positioned along the path of travel of the used sample collector. The movement of the used collector forces the spring-loaded cam to move outwardly. As the used collector is pushed past the high point of the cam, spring 98 returns the cam to its normal position forcing the used collector further along the travel path and into the top entrance 100 of the receiving magazine 94.

Receiving magazine 94 is preferably identical to and interchangeable with supply magazine 70. However, piston 102 (see FIG. 1) of receiving magazine 94 need not be pressurized and simply maintains its position within the receiving magazine through frictional engagement with the side walls thereof.

Another actuator 106, e.g. an air cylinder is mounted above the top opening entrance 100 of receiving magazine 94. A plunger 108 is attached to the lower end of extendable piston 110 of actuator 106. Plunger 108 is retracted from entrance 100 of receiving cylinder 94 when a used sample collector is transferred to the receiving magazine. Thereafter, actuator 106 can be activated to push the used sample collector down into receiving magazine 94 and to close entrance 100 during air sampling. This closer or plunger 108 serves to cover and thereby protect sample collectors in receiving magazine 94 from unwanted contamination, minimize volitization losses and facilitate temperature control, as more fully discussed below.

Like actuator 74 in supply magazine 70, all of the other actuators of changer 14 are preferably pneumatically driven by pump 32 acting as an air compressor, as more fully described hereinafter.

As shown in the pneumatic circuit diagram of FIG. 3, shuttle actuator 88 can be connected to actuator valve train 54 by a computer controlled valve 112. Actuator 22 which controls the movement of lower holder 20 of sampling station 12 and actuator 106 for plunger 108 are connected in parallel through computer controlled valve 114. Actuator valve train 54 also includes a three-way pressure vent valve 116 which cooperates with pump 32 to implement alternate powering of the sampling train and actuator valve train, as more fully discussed below.

In accordance with the principles of the present invention, changer 14 is preferably actuated pneumatically. In order to accomplish this without having a separate air compressor, vacuum pump 32 is valved in such a way that it can switch roles. Three-way vacuum vent valve 52 allows free entry of air into the vacuum side of the pump while disconnecting it from sampling train 30. Simultaneously, three-way pressure vent valve 116, which bypasses the discharge of the pump to atmosphere while in sampling mode, actuates, which connects pump 32 as a compressor to actuator valve train 54. In this way, pump 32 is advantageously utilized to power both sampling and sample collector exchange.

Figure 4:
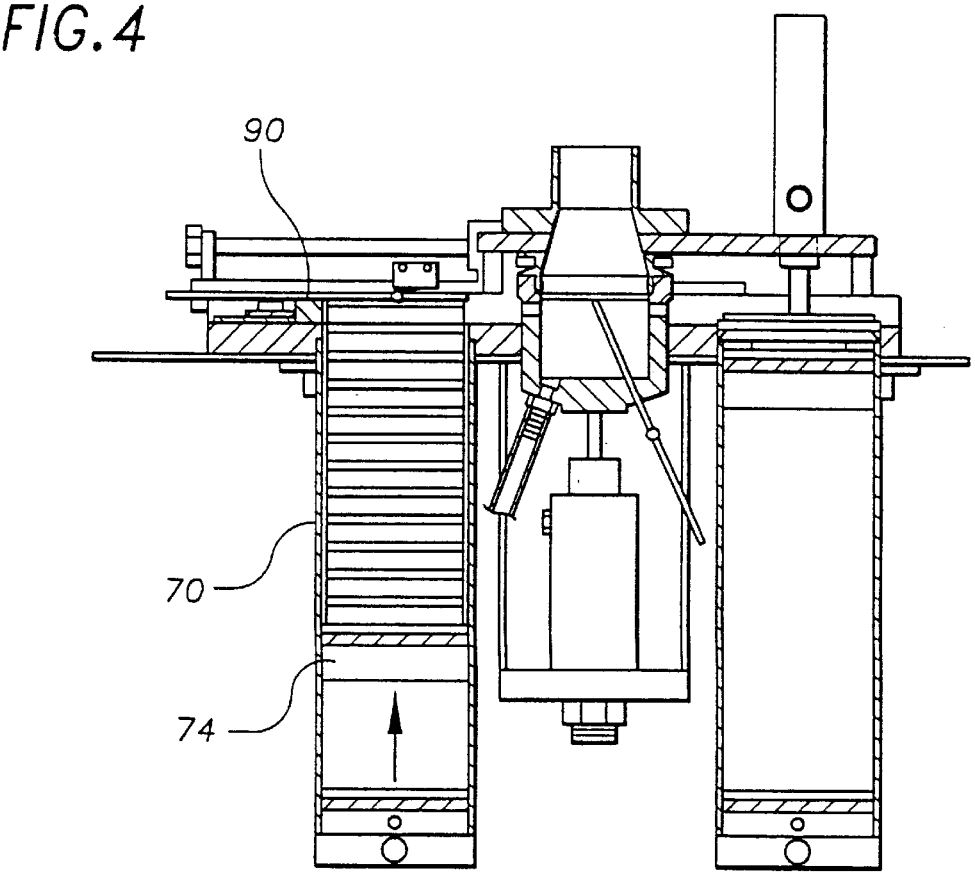
FIG. 4 illustrates the operation of an actuator within the supply magazine of an air sampler constructed in accordance with the principles of the present invention.
Figure 6:
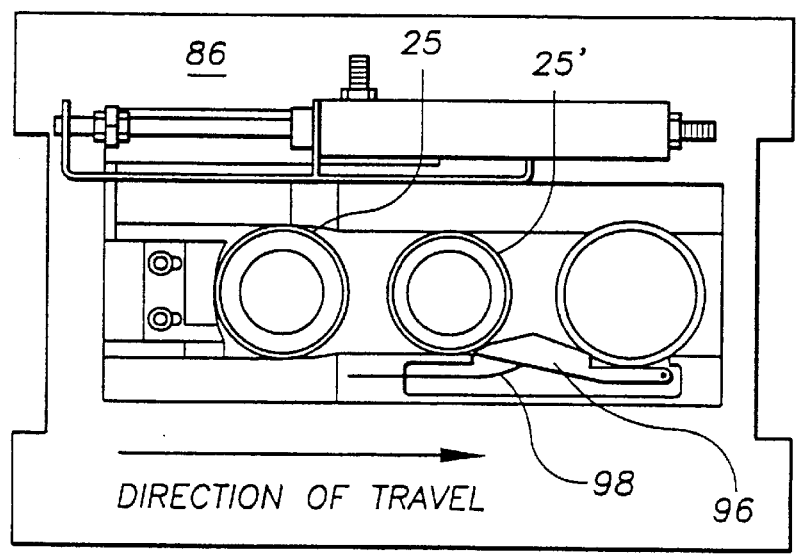
FIG. 6 is a top plan view illustrating the locations of a fresh sample collector and a used sample collector when the transfer mechanism is activated.
Figure 5:
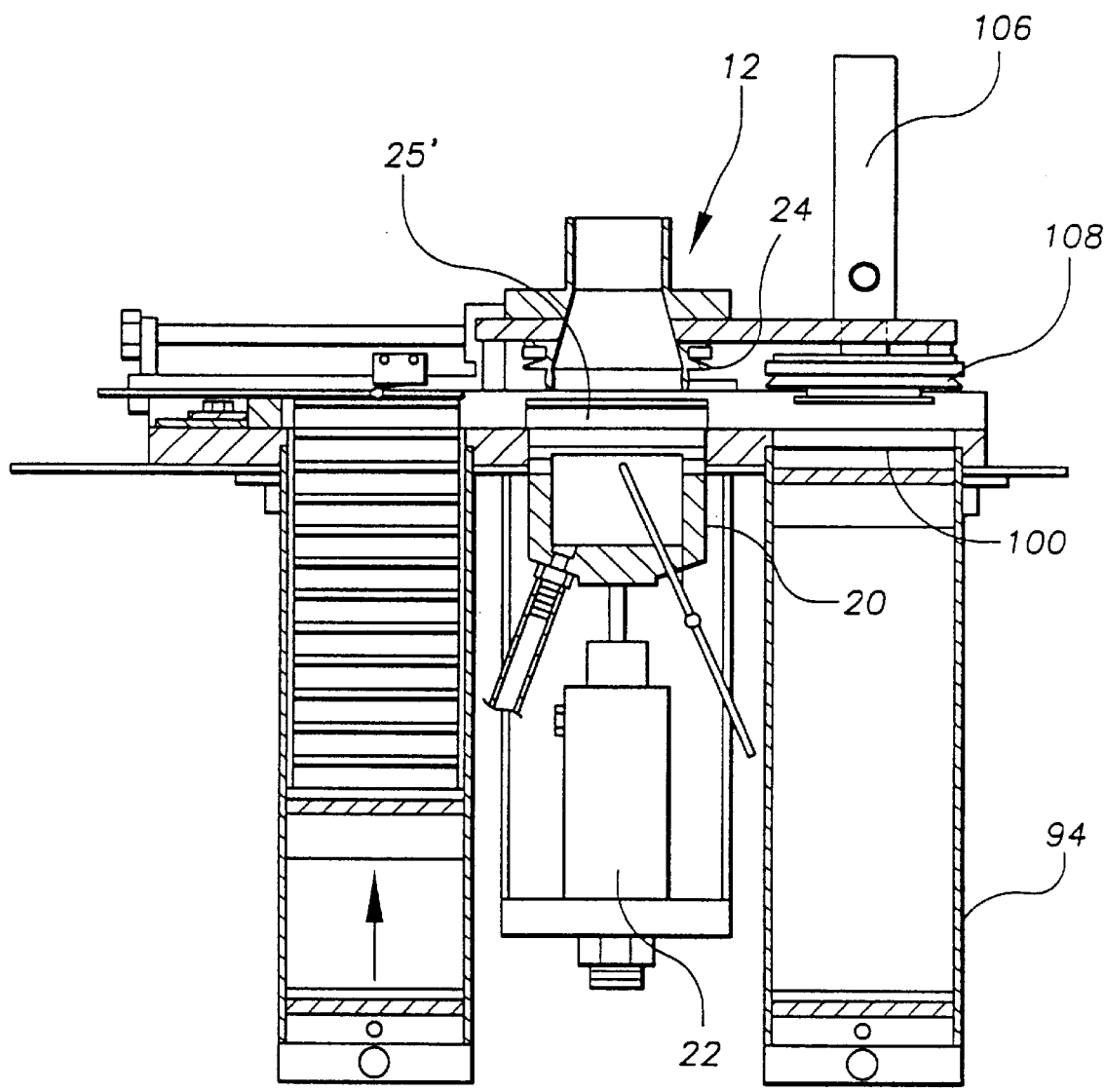
FIG. 5 depicts the operation of other actuators to clear a path for transfer of sample collectors between a supply magazine, sampling station and receiving magazine.
Figure 7:
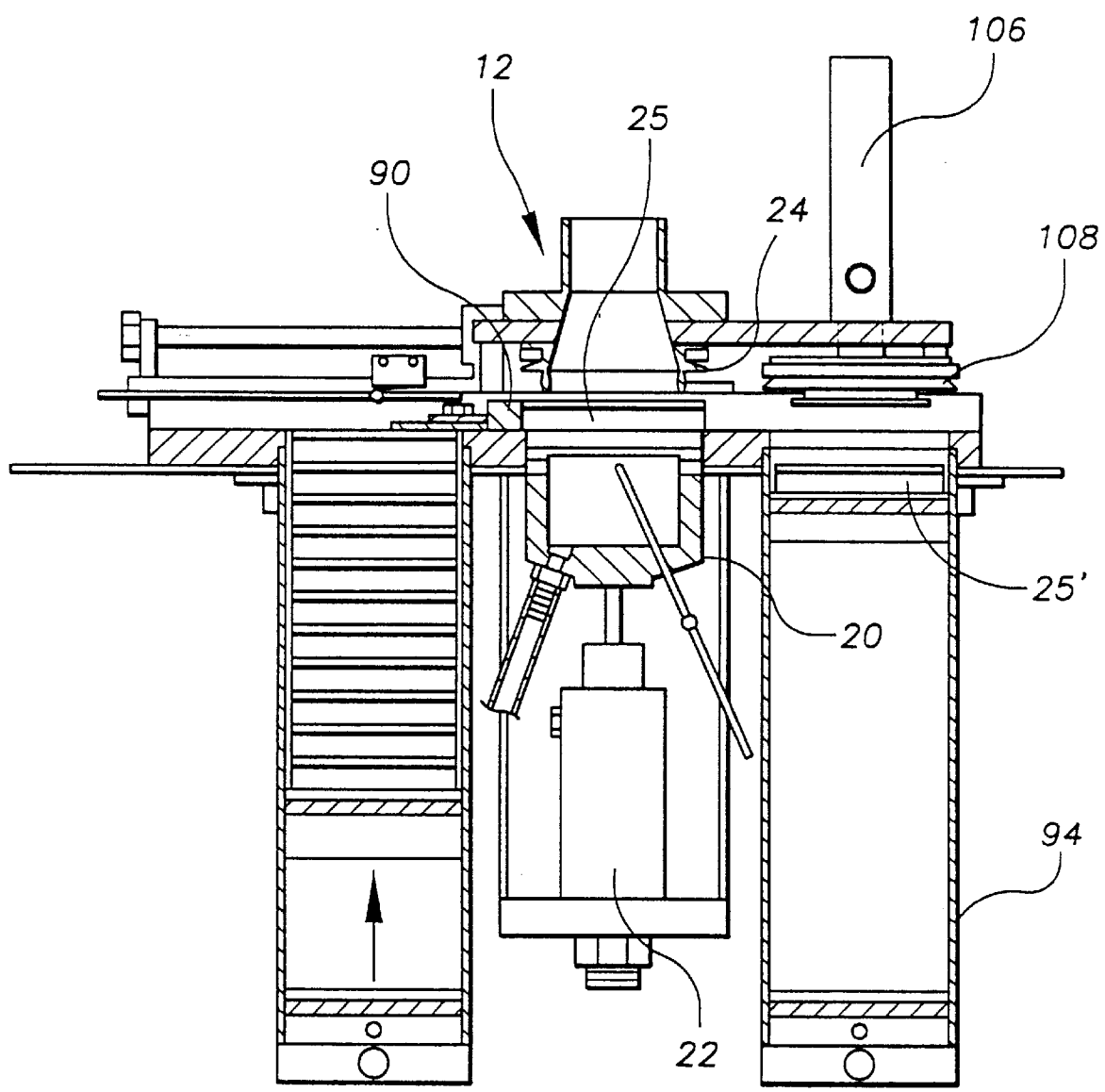
FIG. 7 illustrates the operation of a transfer mechanism.

Sample collector changer 14 utilizes supply magazine 70 and receiving magazine 94 preferably located on opposite sides of sampling station 12. FIG. 1 shows the nominal sampling position of all components. The sample collector changing sequence is illustrated in FIGS. 4–7. All motions are preferably accomplished through pneumatic actuation. In FIG. 4, shuttle 90 is in its "home" position on the far side of the supply magazine 70 and the topmost fresh sample collector 25 is raised to the same level as the shuttle by slight pressurization of the actuator 74 at the lower end of magazine 70. Then, as shown in FIG. 5, lower holder 20 of sampling station 12 is displaced downwardly by actuator 22 to disengage seal 24. Simultaneously actuator 106 raises plunger 108 to uncover the top entrance 100 of receiving magazine 94 in preparation for receipt of a used sample collector 25'. FIG. 7 shows the shuttle 90 retracting, simultaneously pushing a fresh sample collector 25 into the sampling position and positioning the used sample collector 25' over the top entrance of receiving magazine 94. Next actuator 106 lowers the plunger 108, pushing used collector 25' down into receiving magazine 94 and closing the top entrance of the receiving magazine. Concurrently, actuator 22 raises lower holder 20 resulting in a seal around the fresh sample collector 25 in sampling station 12, as shown in FIG. 1. Air flow through sample collector 25 in sampling station 12 is then established and continues for a preprogrammed period of time (typically 24 hours) after which the collector exchange sequence commences again.

Figure 10:
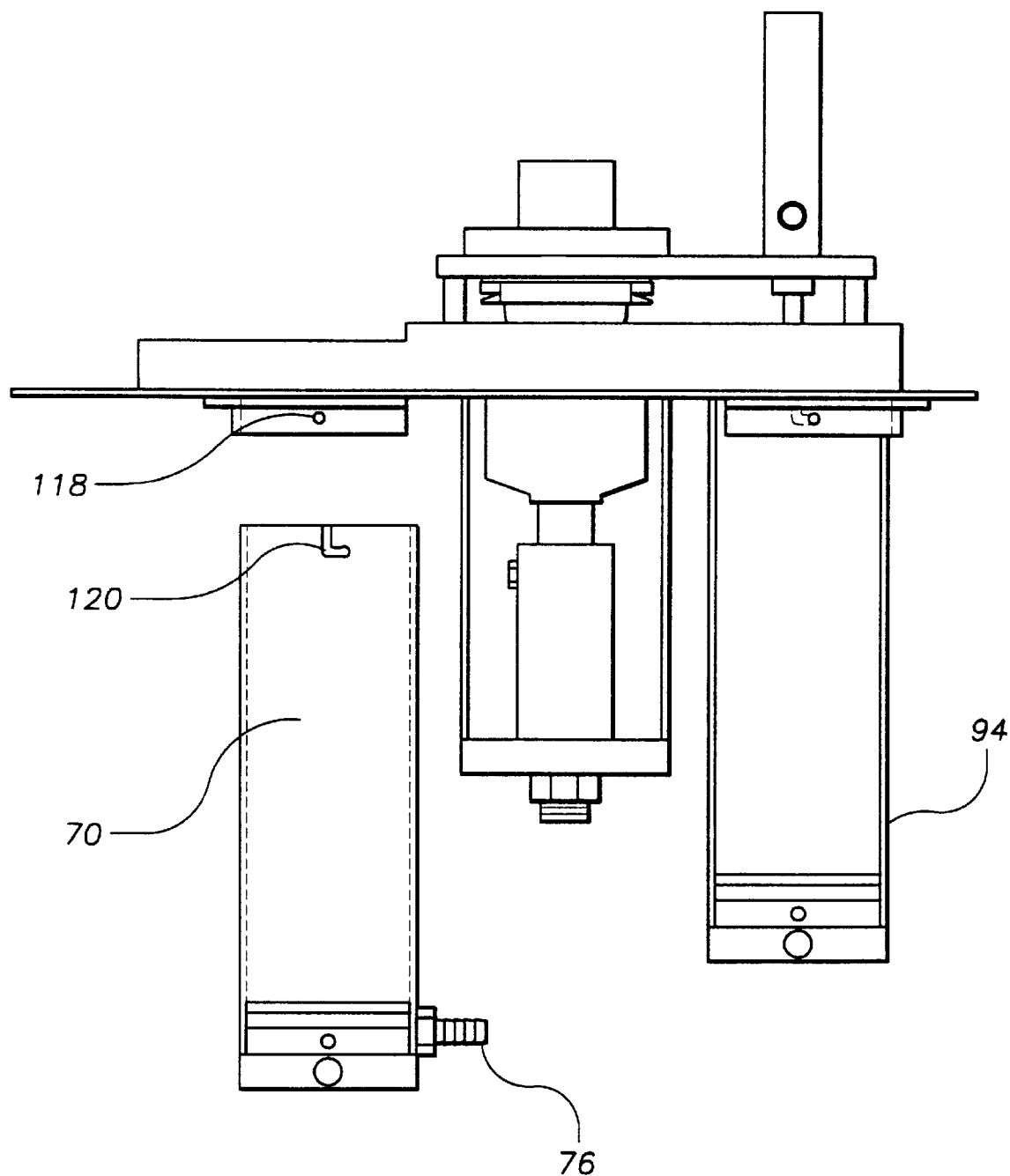
FIG. 10 schematically illustrates the quick connect/disconnect feature and interchangeability of the supply and receiving magazines.

When all of the fresh sample collectors in supply magazine 70 are used, the receiving magazine 94 is easily detached from its mounting and the plunger. The receiving magazine is then sealed with a cap (not shown) and returned to the laboratory for analysis. No handling of individual sample collectors is necessary in the field, thus avoiding sample contamination. The empty supply magazine 70 is also easily detached and can be moved over to become the receiving magazine with its piston already appropriately positioned, while a new supply of sample collectors is provided in a fresh, preloaded supply magazine. A quick connect/disconnect mechanism such as a bayonet lock comprising, as shown in FIG. 10, a mounting pin 118 and a related L-shaped slot 120 on the supply and receiving magazines can be used to rapidly and easily attach and detach the supply and receiving magazines.

The steps of a sample collector change are now presented in detail. Initially, vacuum vent valve 52 is activated to connect the inlet of vacuum pump 32 to atmosphere. This relieves back pressure on the vacuum side of the pump. Pressure vent valve 116 is activated to close the bypass. This builds up pressure in actuator valve train 54. Pressure holds the various actuators of changer 14 in their normal or home position, i.e. shuttle 90 out, lower holder 20 up (in the sampling position) and plunger 108 down. Sensors confirm that all actuators are in the proper positions. FIG. 1 shows this condition.

Supply magazine pressurize valve 80 is then actuated. This pressurizes the actuator 74 in supply magazine 70, lifting the piston and thus the stack 72 of fresh sample collectors. The maximum supply magazine pressure can be limited, for example, to approximately 1.5 psi via relief valve 84. The topmost fresh sample collector 25, rising above the top of supply magazine 70 is stopped by a top plate 91 of the changer. This top collector actuates a sensor, e.g. microswitch 93, proving that the collector is fully up, clear of the supply magazine and in line with the shuttle 90 for the planned transfer. Next, supply magazine pressurize valve 80 is deactivated, releasing the pressure in the actuator 74 of the supply magazine. The cassette stack 72 stays in position due to friction between the piston and the cylinder wall of the supply magazine. (See FIG. 4.)

Next, valve 114 is activated. This lowers holder 20 and raises plunger 108. Sensors confirm that this action has taken place and that the sample collector travel path is now cleared for a collector transfer. (See FIG. 5 and the corresponding top view of FIG. 6)

Shuttle valve 112 is then activated to retract shuttle 90. This moves the shuttle to the IN position which pushes the fresh collector 25 at the top of the supply magazine laterally along the travel path into the sampling position. A sensor can confirm this movement. (See FIG. 7.)

The fresh sample collector moving into the sampling position pushes the previous, now used, sample collector 25' along the travel path toward the receiving magazine. The movement of the used collector forces the spring loaded cam 96 to move outward. As the used collector is pushed past the high point of the cam, cam spring 98 returns the cam to its normal position forcing the used collector further along the path and into the top entrance of the receiving magazine. (See FIG. 7.)

Shuttle valve 112 is then deactivated, returning shuttle 90 to the out (home) position. This movement is preferably confirmed by a sensor. Valve 114 is deactivated causing lower housing 20 to rise and seal the fresh sample collector 25 in the sampling position. Simultaneously, actuator 106 extends the cylindrical plunger on the end of the cylinder rod to push the used sample collector 25' down into the receiving magazine and simultaneously close the entrance of this magazine. Sensors confirm these movements. FIG. 1 shows the resulting configuration of the changer elements. The sample collector change is now complete. In one operative embodiment, the whole change process takes only 10–15 seconds. The vacuum vent valve 52 and pressure vent valve 116 return to their normal position in readiness for the next sampling period to begin. At the command from the controller to begin sampling, the vacuum vent valve 52 activates. This switches the inlet of pump 32 from atmosphere (bypass) to the sampling mode.

Figure 8:
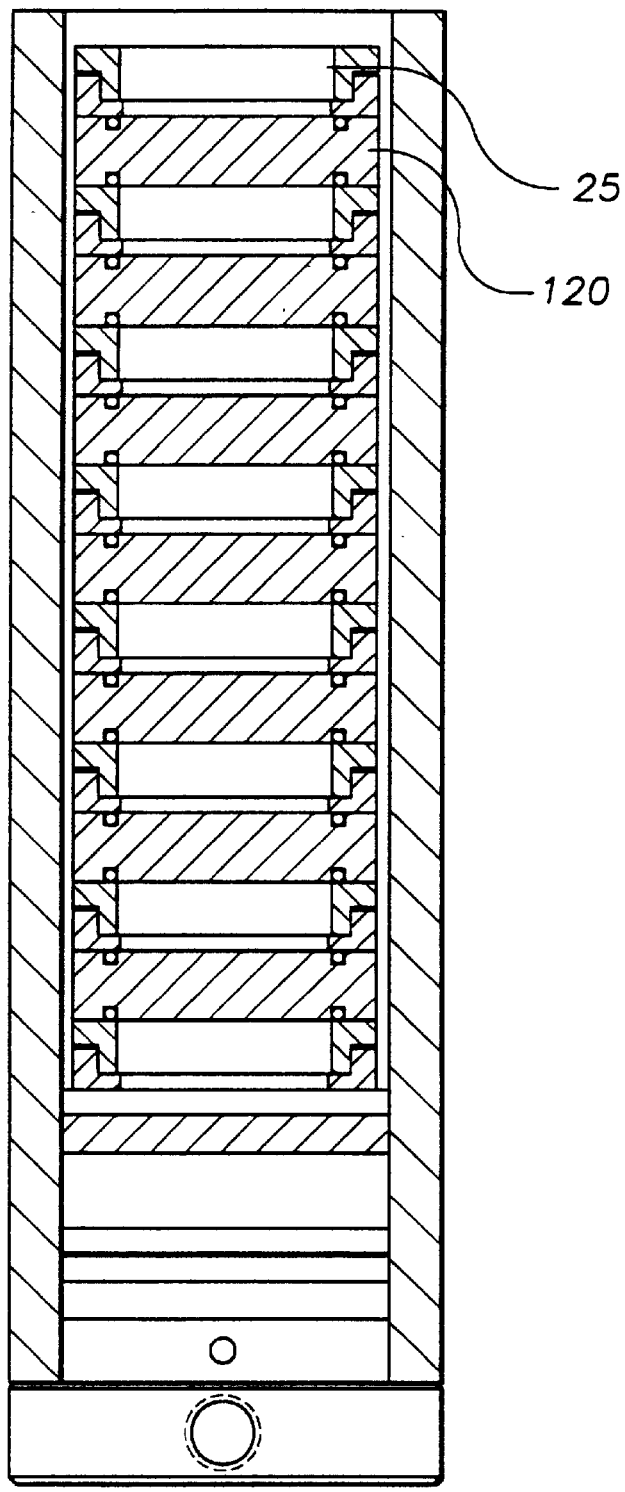
FIG. 8 depicts a magazine with interleaved sample collectors and air impervious covers.
Figure 9:
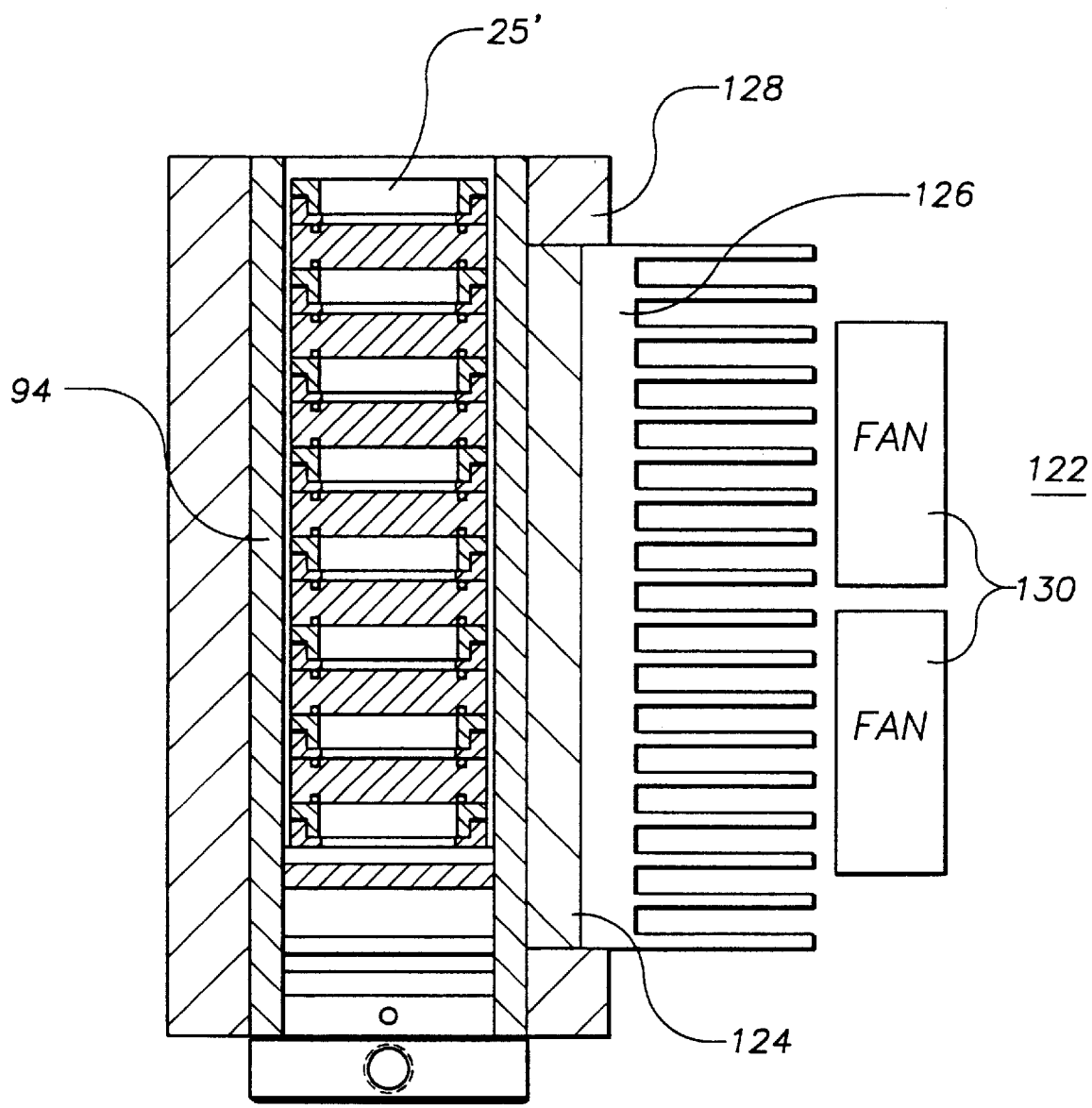
FIG. 9 illustrates a temperature control feature for the receiving magazine.

In order to minimize volitization from used sample collectors and/or for specialized studies where cross contamination of volatile material from the stacked collectors in the receiving magazine needs to be prevented, several alternative arrangements are provided by the present invention. FIG. 8 shows a configuration where air impervious covers 120, e.g. blanks with embedded O-rings or filter cassettes with impermeable material replacing the filter media, are interleaved with sample collectors 25. Operating the air sampler in a mode that transfers a sample collector 25 and a cover 120 after sampling, instead of a single collector, provides a means to isolate each collector in the receiving magazine. This option can be used in concert with or separately from the option shown in FIG. 9. In FIG. 9, the receiving magazine 94, which is closed on both ends, except when receiving a used sample collector during collector transfer, can be maintained at a constant temperature by a temperature controller 122. To preserve volatile material on the used sample collectors 25' in receiving magazine 94, a temperature below ambient air temperature would be chosen, i.e. the receiving magazine would be cooled. This could be accomplished, for example, by use of a thermoelectric cooler 124 in conjunction with heat sink 126, insulation 128 and fans 130.

As will be evident from the above description, this invention provides means to simply, automatically and reliably change sample collectors in an air sampler. In addition, it enables one to keep fresh and used sample collectors in a closed, protected environment, providing ease of collector handling as well as preventing contamination and, in the case of used collectors, to reduce loss of volatile material from the collectors and potential cross-contamination therebetween.

Although preferred embodiments of the invention have been described and depicted herein, it will be evident to those skilled in this art that various modifications, substitutions, additions and the like can be made without departing from the spirit of the invention. For example, multiple supply magazines and/or receiving magazines may be concurrently used in the changer. Further, one of the supply magazines may provide the fresh sample collectors while another supply magazine provides air impervious covers. Although pneumatic actuators are preferred, other types of actuators may also be used. Similarly, variations in the number and nature of the sample collectors and optional covers are possible. For example, instead of filter cassettes, impaction plates might be used as the sample collectors. Blanks or discs with smooth flat surfaces and/or embedded O-rings could be used as the covers. Similarly, variations in the steps and/or sequence of operations are within the scope of this invention.

What is claimed is:

1. An air sampler having an automatic sample collector changer, comprising:

a sampling station for sampling air to collect a sample on a sample collector;

a supply magazine for holding a supply of fresh sample collectors;

a receiving magazine for receiving and storing used collectors from said sampling station following air sampling;

a transfer mechanism for transferring a fresh collector from said supply magazine to the sampling station and a used collector from the sampling station to an entrance of said receiving magazine; and an automatic closer for closing the entrance of said receiving magazine following transfer thereto of a used collector in order to protect the used collector in the receiving magazine from contamination during a subsequent sampling period.

2. The air sampler of claim 1 wherein said closer is separate from said transfer mechanism.

3. The air sampler of claim 1 wherein said closer comprises a plunger located at an end of an actuator.

4. The air sampler of claim 3 wherein said actuator is pneumatically driven by a pump, said pump also serving to draw air into said sampling station for air sampling.

5. The air sampler of claim 1 wherein said automatic closer is pneumatically driven by a pump, said pump also serving to draw air into said sampling station for air sampling.

6. An air sampler having an automatic sample collector changer, comprising:

a sampling station for sampling air to collect a sample on a sample collector;

a supply magazine for holding a supply of fresh sample collectors;

a receiving magazine for receiving and storing used collectors from said sampling station following air sampling; and a transfer mechanism for transferring a fresh sample collector from said supply magazine to the sampling station, a used sample collector from the sampling station to the receiving magazine, and a separate air impervious cover to said receiving magazine.

7. The air sampler of claim 6 wherein said supply magazine holds a stack of interleaved fresh sample collectors and separate air impervious covers.

8. The air sampler of claim 7 wherein said transfer mechanism transfers a used sample collector and one of said air impervious covers to the receiving magazine following air sampling.

9. The air sampler of claim 6 wherein said receiving magazine receives and stores used sample collectors in a stack with interspersed separate air impervious covers.

10. A sequential air sampler having an automatic sample collector changer, comprising:

a sampling station for sampling air to collect a sample on a sample collector;

a supply magazine for holding a supply of fresh sample collectors;

a receiving magazine for receiving and storing used collectors from said sampling station following air sampling; and a transfer mechanism for transferring a fresh sample collector from said supply magazine to the sampling station, said transferring fresh sample collector displacing a used sample collector out of said sampling station towards an entrance of said receiving magazine.

11. The air sampler of claim 10 wherein said transfer mechanism includes a pivotally mounted spring-loaded kicker cam to transfer a displaced used sample collector to the entrance of the receiving magazine.

12. An air sampler having an automatic sample collector changer, comprising:

a sampling station for sampling air to collect a sample on a sample collector;

a supply magazine for holding a supply of fresh sample collectors;

a receiving magazine for receiving and storing used collectors from said sampling station following air sampling;

a transfer mechanism for transferring a fresh collector from said supply magazine to the sampling station and a used collector from the sampling station to an entrance of said receiving magazine; and a temperature controller adjacent the receiving magazine for maintaining used collectors in the receiving magazine at a set temperature.

13. The air sampler of claim 12 wherein said temperature controller maintains the used collectors in the receiving magazine at a set temperature below ambient air temperature to reduce volatization losses.

14. The air sampler of claim 13 wherein said temperature controller includes a thermoelectric cooler.

15. A sequential air sampler having an automatic sample collector changer, comprising:

a sampling station for sampling air to collect a sample on a sample collector;

a supply magazine for holding a stack of fresh sample collectors;

a receiving magazine for receiving and storing used sample collectors from said sampling station following air sampling;

a transfer mechanism for transferring a fresh sample collector from said supply magazine to said sampling station and a used sample collector from the sampling station to the receiving magazine;

an actuator located within said supply magazine for displacing said stack in order to position a fresh sample collector at an uppermost end of said stack for transfer by said transfer mechanism; and a sensor for confirming proper positioning of the fresh sample collector at the uppermost end of said stack for transfer by said transfer mechanism.

16. The air sampler of claim 15 wherein said supply magazine comprises a cylindrical canister, said actuator comprises a piston located within said canister, and wherein, after transfer of a last collector of said stack of fresh sample collectors by the transfer mechanism, the supply magazine replaces the receiving magazine with the piston inherently appropriately positioned to receive a used sample collector from the sampling station.

* * * * *